US008655456B2

(12) United States Patent
Ranu (10) Patent No.: US 8,655,456 B2
(45) Date of Patent: Feb. 18, 2014

(54) SYSTEMS AND METHODS FOR ANCHORING LEADS OF ELECTRICAL STIMULATION SYSTEMS

(71) Applicant: Boston Scientific Neuromodulation Corporation, Valencia, CA (US)

(72) Inventor: Emant Ranu, Fort Collins, CO (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/650,449

(22) Filed: Oct. 12, 2012

(65) Prior Publication Data

US 2013/0096659 A1  Apr. 18, 2013

Related U.S. Application Data

(60) Provisional application No. 61/546,633, filed on Oct. 13, 2011.

(51) Int. Cl.
*A61N 1/05* (2006.01)
(52) U.S. Cl.
USPC .......................................................... 607/116
(58) Field of Classification Search
USPC ........................................... 607/45, 115–116
See application file for complete search history.

(56) References Cited

U.S. PATENT DOCUMENTS

| | | |
|---|---|---|
| 7,809,446 B2 | 10/2010 | Meadows |
| 2007/0150036 A1 | 6/2007 | Anderson |
| 2009/0118804 A1* | 5/2009 | Moffitt et al. ................ 607/116 |
| 2009/0187222 A1 | 7/2009 | Barker |
| 2009/0276021 A1 | 11/2009 | Meadows et al. |
| 2010/0076535 A1 | 3/2010 | Pianca et al. |

OTHER PUBLICATIONS

U.S. Appl. No 2/177,823, filed Jul. 22, 2008.
U.S. Appl. No. 61/170,037 filed Apr. 16, 2009.
U.S. Appl. No. 61/022,953, filed Jan. 23, 2008.
U.S. Appl. No. 61/316,759, filed Mar. 23 2010.

* cited by examiner

*Primary Examiner* — Rex R Holmes
(74) *Attorney, Agent, or Firm* — Frommer Lawrence & Haug LLP; Bruce E. Black (57) ABSTRACT

A lead anchor assembly includes a burr hole cover that defines a first lead aperture in a side exterior surface, a second lead aperture in a bottom exterior surface, and a fastener aperture. An anchoring unit is disposed in the burr hole cover and includes a fastener for anchoring a lead to the burr hole cover. A lead pathway is defined through the burr hole cover and the anchoring unit. The lead pathway extends from the first lead aperture to the second lead aperture and is configured to receive a lead. A fastener pathway is defined through both the burr hole cover and the anchoring unit and intersects the lead pathway at an anchoring location. The fastener pathway is configured for movement of the fastener along the fastener pathway to engage and disengage the lead when the lead extends along the lead pathway across the anchoring location.

20 Claims, 5 Drawing Sheets

SYSTEMS AND METHODS FOR ANCHORING LEADS OF ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/546,633 filed on Oct. 13, 2011, which is incorporated herein by reference.

FIELD

The invention is directed to the area of electrical stimulation systems and methods of making and using the systems. The present invention is also directed to electrical stimulation leads and anchoring units for fixing the leads within a patient, as well as methods of making and using the leads, anchoring units, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, a lead anchor assembly includes a burr hole cover configured and arranged for implanting over a burr hole formed in a skull of a patient. The burr hole cover has a top exterior surface, an opposing bottom exterior surface, and a side exterior surface coupling the top exterior surface to the bottom exterior surface. The burr hole cover defines a first lead aperture in the side exterior surface, a second lead aperture in the bottom exterior surface, and a fastener aperture. An anchoring unit is disposed in the burr hole cover and includes a fastener configured and arranged for anchoring a lead to the burr hole cover. A lead pathway is defined through the burr hole cover and the anchoring unit. The lead pathway extends from the first lead aperture to the second lead aperture and is configured and arranged to receive a lead. A fastener pathway is defined through both the burr hole cover and the anchoring unit and intersects the lead pathway at an anchoring location. The fastener pathway is configured and arranged for movement of the fastener along the fastener pathway to engage and disengage the lead when the lead extends along the lead pathway across the anchoring location.

In another embodiment, an implantable electrical stimulation system includes a lead having a proximal end and a distal end. The lead includes a plurality of terminals disposed at the proximal end of the lead and a plurality of electrodes disposed at the distal end of the lead. A burr hole cover configured and arranged for implanting over a burr hole formed in a skull of a patient. The burr hole cover has a top exterior surface, an opposing bottom exterior surface, and a side exterior surface coupling the top exterior surface to the bottom exterior surface. The burr hole cover defines a first lead aperture in the side exterior surface, a second lead aperture in the bottom exterior surface, and a fastener aperture. An anchoring unit is disposed in the burr hole cover and includes a fastener configured and arranged for anchoring the lead to the burr hole cover. A lead pathway is defined through the burr hole cover and the anchoring unit. The lead pathway extends from the first lead aperture to the second lead aperture. The lead pathway is configured and arranged to receive the lead. A fastener pathway is defined through both the burr hole cover and the anchoring unit and intersects the lead pathway at an anchoring location. The fastener pathway is configured and arranged for movement of the fastener along the fastener pathway to engage and disengage the lead when the lead extends along the lead pathway across the anchoring location.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to electrical stimulation leads and anchoring units for fixing the leads within a patient, as well as methods of making and using the leads, anchoring units, and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, and U.S. Patent Application Publication No. 2009/0187222 A1. Each of these references is incorporated herein by reference in its respective entirety.

Figure 1:
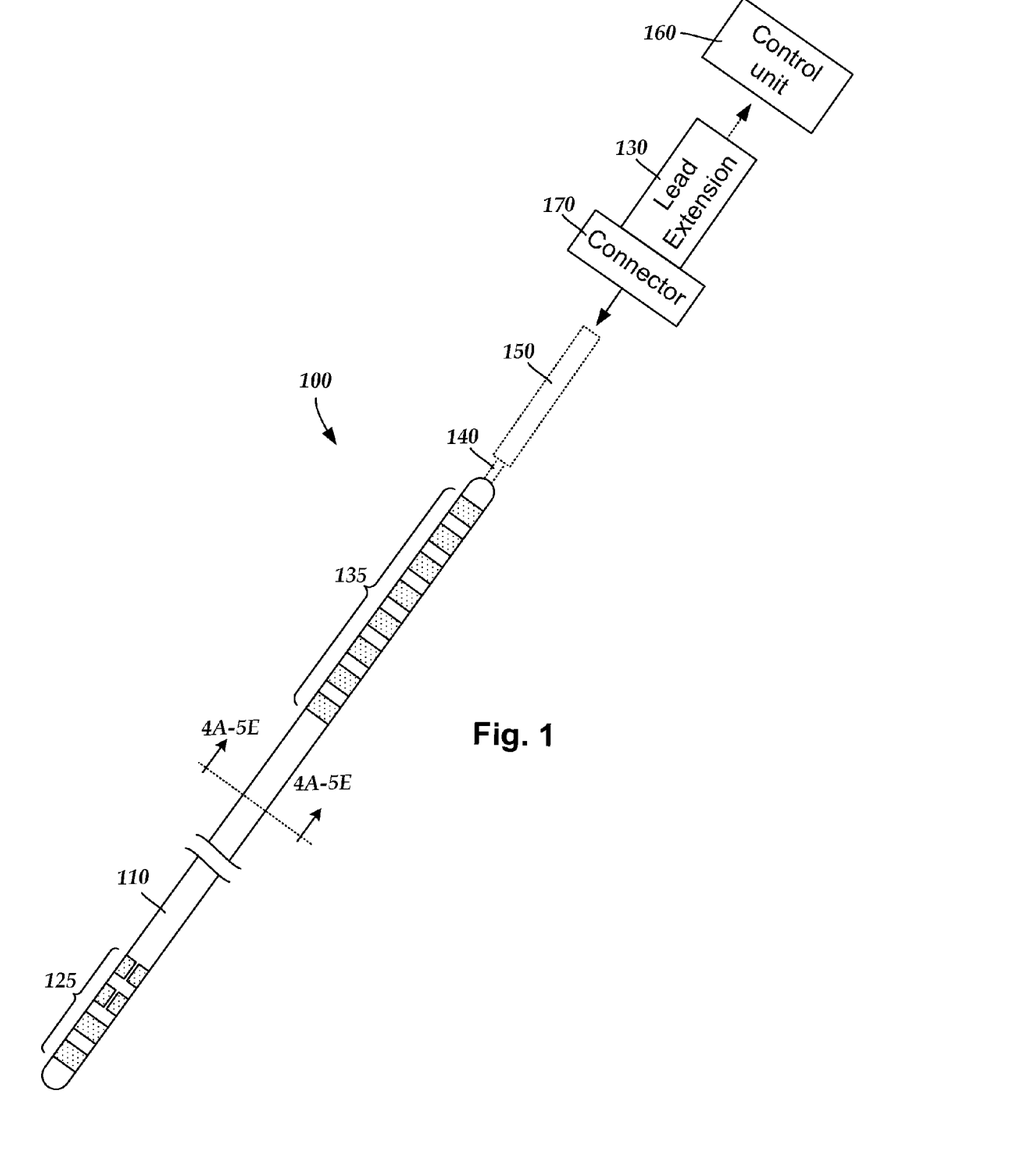
FIG. 1 is a schematic side view of one embodiment of a brain stimulation system that includes a lead, a lead extension, and a control unit, according to the invention.

FIG. 1 illustrates one embodiment of an electrical stimulation system 100 for brain stimulation. The electrical stimulation system 100 includes a lead 110, a plurality of electrodes 125 disposed at least partially about a circumference of the lead 110, a plurality of terminals 135, a lead extension 130 for connection of the electrodes 125 to a control unit 160, and a stylet 140 for assisting in insertion and positioning of the lead 110 within the patient's skull (e.g., in the patient's brain). It may be advantageous to include the lead extensions 130 to prevent having to remove or replace the lead 110 if the proximal end of the lead 110 fails due to fatigue (e.g., from flexing of the patient's neck, or the like).

The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The lead extension 130 includes a connector 170 that fits over a proximal end of the lead 110, preferably after removal of the stylet 140.

The control unit 160 is typically an implantable pulse generator that can be implanted into a patient's body, for example, below the patient's clavicle area. The pulse generator can have eight stimulation channels which may be independently programmable to control the magnitude of the current stimulus from each channel. In some cases, the pulse generator may have more than eight stimulation channels (e.g., 16-, 32-, or more stimulation channels). The control unit 160 may have one, two, three, four, or more connector ports, for receiving the plurality of terminals 135 at the proximal end of the lead 110.

In one example of operation, access to the desired stimulation location in the brain can be accomplished by drilling a hole in the patient's skull or cranium with a cranial drill (commonly referred to as a "burr" or "bur"), and coagulating and incising the dura mater, or brain covering. The lead 110 can be inserted into the cranium and brain tissue with the assistance of the stylet 140. The lead 110 can be guided to the target stimulation location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 has a cross-sectional diameter of no more than 1.5 mm and may be in the range of 1 to 1.5 mm. In at least some embodiments, the lead 110 is rotatable so that the stimulation electrodes can be aligned with the target neurons after the neurons have been located using the recording electrodes. Stimulation electrodes may be disposed on the circumference of the lead 110 to stimulate the target neurons. Stimulation electrodes may be ring-shaped or segmented.

The lead extension 130 typically couples the electrodes 125 to the control unit 160 (which typically houses a pulse generator that supplies electrical signals to the electrodes 125). Connectors of conventional lead extensions are typically disposed within patient tissue such that the connectors are disposed over the patient's skull and beneath or within the patient's scalp above one of the patient's ear.

As discussed above, during implantation the distal end of the lead is typically inserted into a burr hole in the patient's skull and positioned such that the electrodes are disposed at a target stimulation location (e.g., the sub thalamic nucleus, the globus pallidus interna, the ventral intermediate nucleus, or the like). Meanwhile, a proximal end of the lead is disposed external to the patient's skull and is typically coupled to a connector of a lead extension or control unit. In at least some cases, a burr hole cover (e.g., a burr hole cover or cap, bone cement, one or more mini-plates, or the like) is disposed over the burr hole, and the distal portion of the lead extends through the burr hole cover, into the patient's brain.

Once the distal end of the lead is implanted inside the patient's skull, it may be desirable to reduce, or even eliminate, movement of the distal end of the lead relative to the patient. As herein described, the burr hole cover ("cover") includes an anchoring unit for anchoring a portion of the lead to the cover when the lead is extended through the cover. The anchoring unit reduces, or even prevents, movement of the lead on one side of the cover from causing corresponding movement of the lead on the opposing side of the cover. Thus, when the cover is disposed over a burr hole and a lead is extended through the cover such that a distal end of the lead is disposed in a patient's skull and a proximal end of the lead is disposed external to the patient's skull, the anchoring unit reduces, or even prevents, movement of the lead external to the cover from causing corresponding movement of the lead disposed within the patient's skull.

Figure 2A:
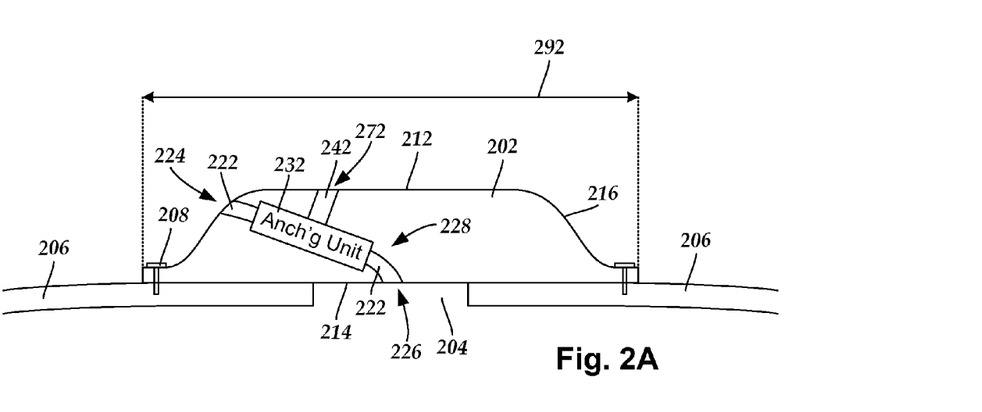
FIG. 2A is a schematic cross-sectional view of one embodiment of a lead pathway defined through both a burr hole cover and an anchoring unit disposed in the burr hole cover along the lead pathway, the burr hole cover positioned over a burr hole formed in a skull of a patient, according to the invention.
Figure 2B:
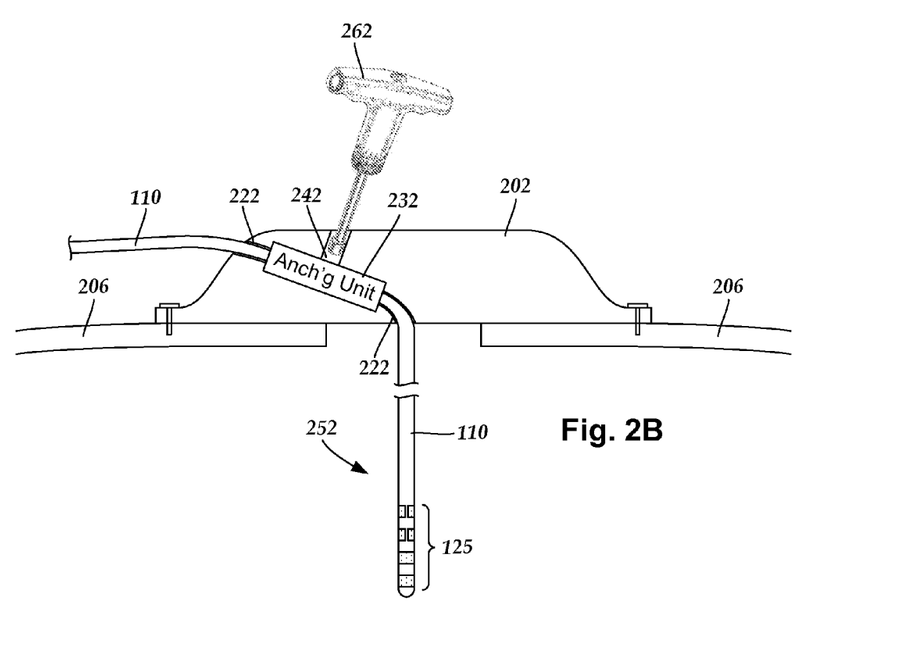
FIG. 2B is a schematic cross-sectional view of one embodiment of a lead disposed in the lead pathway of FIG. 2A, the lead pathway defined through both the burr hole cover and the anchoring unit of FIG. 2A, the lead fixable to the anchoring unit using a tool to tighten the lead against the anchoring unit, according to the invention.

FIG. 2A is a schematic cross-sectional view of one embodiment of a cover 202 disposed over a burr hole 204 formed in a cranial bone 206 of a patient. FIG. 2B is a schematic cross-sectional view of one embodiment of a distal end 252 of the lead 110 extending through the cover 202 and into the burr hole 204 such that the electrodes 125 are disposed within the patient's brain. The cover 202, optionally, can be coupled to the cranial bone 206 at one or more locations using, for example, one or more fasteners (e.g., screws, pins, or the like or combinations thereof), such as fastener 208. In at least some embodiments, adhesive may be used in lieu of, or in addition to, the one or more fasteners 208.

The cover 202 can have any shape suitable for disposing the cover 202 over the burr hole and, when applicable, disposing the cover 202 beneath patient skin. The cover 202 has a top exterior surface 212, an opposing bottom exterior surface 214, and at least one side exterior surface 216 coupling the top exterior surface 212 to the bottom exterior surface 214. In at least some embodiments, the bottom exterior surface 214 is substantially planar. In at least some embodiments, the bottom exterior surface 214 is substantially planar and extends parallel to the top exterior surface 212. The cover 202 can be manufactured either as a single component or as multiple components configured and arranged for coupling together for implantation.

A lead pathway 222 extends along the cover 202 between a first lead aperture 224 and a second lead aperture 226. The lead pathway 222 is configured and arranged to receive (e.g., slidably receive) the lead. The lead pathway 222 can be formed in any suitable manner for housing the lead within the cover 202. In at least some embodiments, the lead pathway 22 is formed as one or more lumens. The lead pathway 222 may have a cross-section that is substantially circular as it extends from the first lead aperture 224 to the second lead aperture 226. It is contemplated that the lead pathway 222 may also have a cross-section in the shape of a triangle, a square, an ovoid, or any other suitable shape that is large enough to house the lead 110.

In at least some embodiments, the first lead aperture 224 of the lead pathway 222 is defined along the side exterior surface 216 of the cover 202. In at least some embodiments, the second opening 226 of the lead pathway 222 is defined along the bottom exterior surface 214 of the cover 202. As mentioned above, after implantation of the lead, skin may be laid over the cover 202. Accordingly, it may be desirable for the cover 202 to have a low profile to enable the patient's skin to fit over the cover 202. It may, therefore, be advantageous for the first lead aperture 224 to be defined along the side exterior surface 216 instead of the top exterior surface 212 so that, when the lead is inserted into the lead pathway 222, the portion of the lead extending outwardly from the first lead aperture 224 does not extend directly into the patient's skin, but rather extends along an underside of the patient's skin.

In at least some embodiments, the lead pathway 222 forms a bend 228. In at least some embodiments, the lead pathway 222 forms a single bend 228. The bend 228 can be any suitable angle for enabling the lead, when disposed in the lead pathway 222, to transition from extending along an exterior surface of the cranial bone 206 (and, in some cases, beneath patient skin) to extending through the burr hole 204 (see FIG. 2B). The bend 228 can have any suitable arc including, for example, at least 20°, 25°, 30°, 35°, 40°, 45°, 50°, 55°, 60°, or more. The bend 228 is preferably a gradual curve having a radius of curvature that is at least one-fifth, one-quarter, one-third, or more of a diameter 292 of the cover 202.

An anchoring unit 232 is disposed in the cover 202. The anchoring unit 232 is disposed along a portion of the lead pathway 222 at an anchoring location (380 in FIG. 3A). The anchoring unit 232 can be disposed in the cover 202 in any suitable manner. In at least some embodiments, the anchoring unit 232 is integral with the cover 202 such that the anchoring unit 232 forms a continuous unit with the cover 202. For example, the anchoring unit 232 and the cover 202 may be manufactured together as a single, inseparable unit. In some cases, the anchoring unit 232 and the cover 202 may be manufactured together such that there is no distinct separation between the anchoring unit 232 and the cover 202.

In alternate embodiments, the anchoring unit 232 a stand-alone unit that may be coupled to the cover 202, or one or more portions thereof, either removably or permanently. In at least some embodiments, the anchoring unit 232 is configured and arranged to receive a single lead. In alternate embodiments, the anchoring unit 232 is configured and arranged to receive a plurality of leads. In at least some embodiments, two or more anchoring units 232 may be disposed in the cover 202.

In at least some embodiments, when a portion of the lead 110 is disposed in the lead pathway 222, the anchoring unit 232 includes a fastener (320 in FIG. 3A) that holds the lead in place by compressing the lead 110 at the anchoring location. In which case, the cover 202 defines a fastener pathway 242 for enabling a tool 262 to access the fastener. The fastener pathway 242 extends from a fastener aperture 272 defined along one of the exterior surfaces 212, 214, or 216 to an anchoring location (380 in FIG. 3A). The tool 262 may be used to move the fastener along the fastener pathway's 242 to engage or disengage the lead. Engagement of the lead 110 with the fastener anchors the lead 110 to the cover 202. The tool 262 may be a screwdriver, wrench, pliers, or drill or any other suitable tool useful for setting, fixing, screwing, tightening, fastening or fitting the fastener against the lead 110. In at least some embodiments, the tool 262 is a torque limiting tool set to a certain threshold above which it will no longer tighten the fastener. With this tool, over-tightening of the fastener is avoided and the lead can be protected from possible damage due to over-tightening the fastener. For example, the torque limiting tool may be configured to limit the number of revolutions or the depth to which the fastener may be advanced.

Figure 3A:
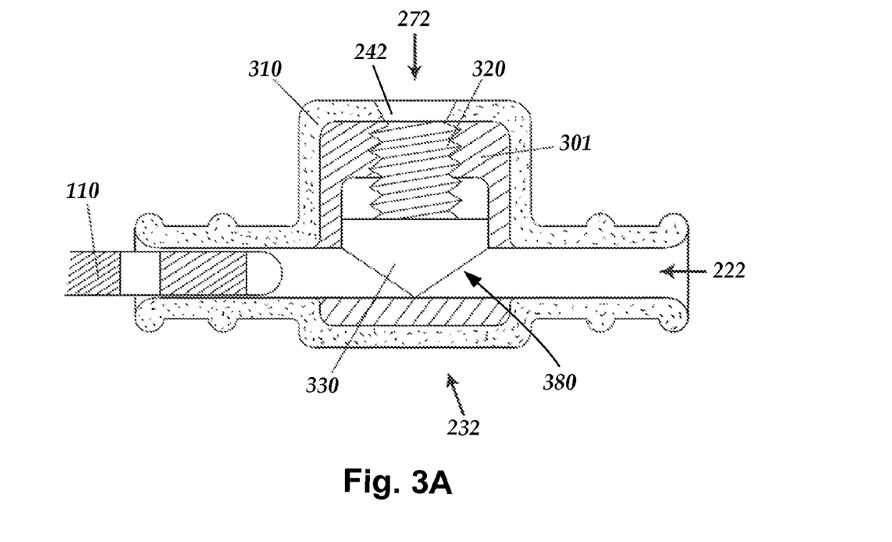
FIG. 3A is a schematic cross-sectional view of one embodiment of an anchoring unit with a pressure plate, according to the invention.

As mentioned above, the anchoring unit can either be integral with the cover 202 or be a stand-alone unit coupleable with the cover 202. FIGS. 3A-6 show the anchoring unit 232 as a stand-alone unit, for ease of illustration. FIG. 3A is a schematic cross-sectional view of one embodiment of the anchoring unit 232. As shown in FIG. 3A, the anchoring unit 232 includes a body 301 and an exterior member 310. In embodiments where the anchoring unit 232 is formed integrally with the cover 202, the anchoring unit 232 may or may not have a body 301 or an exterior member 310 (or both) that is separable or distinct from the cover 202.

The body 301 may be made of a metal, such as titanium, nickel, aluminum, stainless steel, copper, gold, silver, platinum and alloys thereof or any other biocompatible metal, or a rigid plastic or polymer material. The exterior member 310 may be formed of any biocompatible material such as plastics and polymers including, but not limited to, silicone, polyvinyl chloride, fluoropolymers, polyurethane, polycarbonate, acrylic compounds, thermoplastic polyesters, polypropylene, low-density polyethylenes, and other thermoplastic elastomers. In some embodiments, the exterior member 310 is made of silicone. In some embodiments, the exterior member 310 and the body 301 are made of the same material. In some embodiments, the exterior member 310 and the body 301 are unitary. In at least some embodiments, the body 301 is unitary with the cover 202. In at least some embodiments, the body 301, exterior member 310, and the body 301 are all unitary.

Furthermore, it may be useful for any or all parts of the anchoring unit 232 to be made of a material that is radiopaque, so that it is visible under fluoroscopy or other forms of x-ray diagnosis. In some embodiments, the body or the exterior member (or one or more other parts of the anchoring unit) is radiopaque so as to allow the anchoring unit to be readily identified under fluoroscopy or other forms of x-ray diagnosis. The lead itself may also be radiopaque.

The anchoring unit 232 is disposed along a portion of the lead pathway 222 at an anchoring location 380. In some embodiments, the anchoring unit 232 defines more than one lead pathway 222 so that the anchoring unit 232 is able to house more than one lead. At the anchoring location 380, the lead pathway 222 may be a friction fit with the lead 110 or can be large enough to enable the lead 110 to pass through freely. In some embodiments, the portion of the lead pathway 222 at anchoring location 380 is formed of a tapped and reamed-through lumen.

The fastener pathway 242 may have a cross-section that is substantially circular. In other embodiments, the fastener pathway 242 has a cross-section in the shape of a triangle, a square, an ovoid, or any other suitable shape that is capable of housing the fastener 320. In some embodiments, the fastener pathway 242 is positioned perpendicular to the lead pathway 222 at the anchoring location 380. In other embodiments, the fastener pathway 242 may be defined so that the fastener 320 engages the lead 110 within the lead pathway 222 approximately (or exactly) at a 15, 30, or 45 degree angle or any other suitable angle with respect to a central axis of the lead pathway 222 at the anchoring location 380.

In at least some embodiments, the fastener aperture 272 is defined in the top exterior surface 272 of the cover 202. In which case, the fastener pathway 242 may extend from the fastener aperture 272 in a direction that is perpendicular to the top exterior surface 212 of the cover 202. In other embodiments, the fastener pathway 242 may extend from the fastener aperture 272 in a direction that is approximately (or exactly) at a 15, 30, or 45 degree angle or any other suitable angle with respect to the top exterior surface 212.

In some embodiments, the fastener pathway 242 intersects the lead pathway 222 and extends through the lead pathway 222 so that a cross-shaped void is formed at the anchoring location 380. In at least some embodiments, the fastener pathway 242 merges with the lead pathway 222 but does not extend through the lead pathway 222, so that the cross-section of the anchoring unit 232 defines a T-shaped bore at the anchoring location 380. In at least some embodiments, the anchoring unit 232 includes a sleeve or a pressure plate disposed at the anchoring location 380 (see, e.g., FIGS. 5 and 6) for facilitating anchoring of the lead. In embodiments with multiple lead pathways 222, the anchoring unit 232 may define more than one fastener pathway 242 for receiving a plurality of fasteners 320. Additionally, the anchoring unit 232 may include a thread, groove, crease, channel, duct, or rib disposed along one or more portions of inner walls of the fastener pathway 242 for facilitating anchoring of the lead.

The fastener 320 may be, for example, a pin, clamp, latch, lug, nail, bolt, dowel, rod, rivet, screw or any combination thereof or any other suitable item for engaging and anchoring the lead. The fastener 320 may engage or couple to the anchoring unit 232 by any method such as, for example, tightening, screwing or pushing. In some embodiments, the fastener 320 is a set screw with a thread. In which case, the anchoring unit 232 may include a thread complementary to the thread of the set screw disposed along at least a portion of the fastener pathway 242. As described above, with reference to FIG. 2B, the set screw may be tightened through the use of the tool 262. As the fastener 320 engages the anchoring unit 232 through the fastener pathway 242, the fastener 320 is brought closer to the lead pathway 222.

In some embodiments, the fastener 320 engages a pressure plate 330 positioned at the anchoring location 380. As the fastener 320 is tightened, the pressure plate 330 is moved within the anchoring unit 232 to at least partially obstruct the lead pathway 222. When the lead 110 is disposed within the lead pathway 222 and the fastener 320 is tightened, the pressure plate 330 closes down on the lead 110 to keep the lead 110 in place.

Figure 3B:
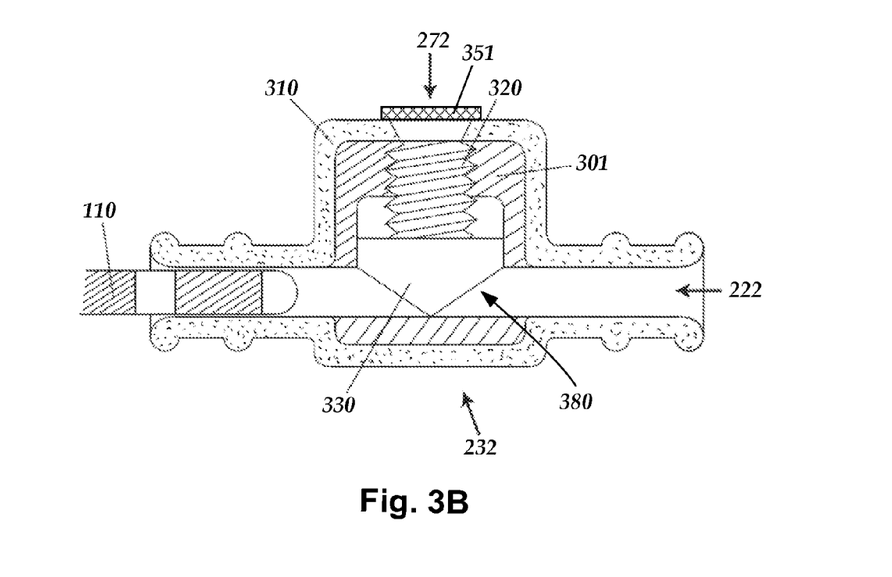
FIG. 3B is a schematic cross-sectional view of another embodiment of the anchoring unit of FIG. 3A with a septum, according to the invention.
Figure 4:
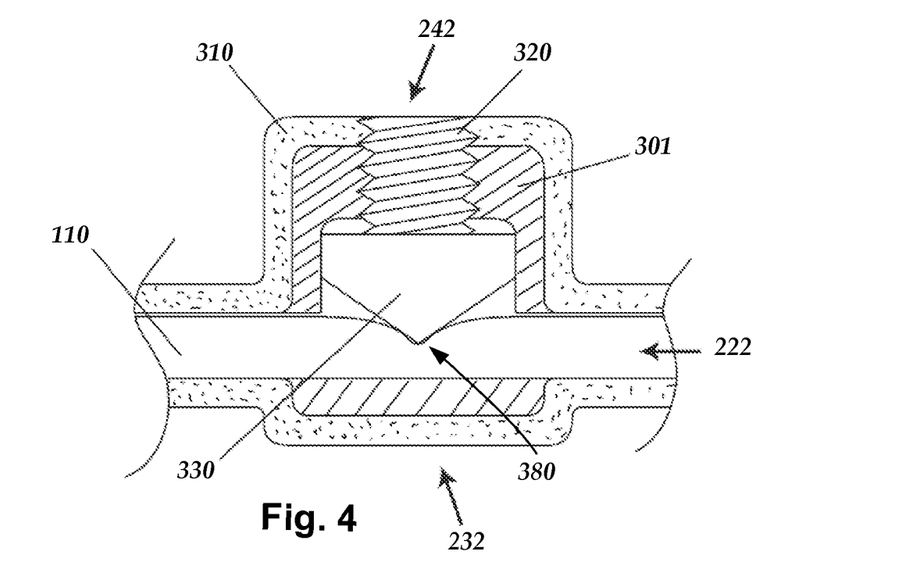
FIG. 4 is a schematic cross-sectional view of the anchoring unit of FIG. 3A after a lead has been inserted in the anchoring unit, according to the invention.

As shown in FIGS. 3A-4, in some embodiments the cross section of the pressure plate 330 may be in the shape of a triangle. Alternatively, the cross-section of the pressure plate 330 may be in the shape of a circle, an ovoid, a rectangle, or any other suitable shape. In at least some embodiments, the lead 110 is deformed when the pressure plate 330 is brought into position. In some embodiments, the deformation is slight (e.g., no more than 5% or 10% of the thickness of the lead). In other embodiments, the deformation is more significant (e.g., at least 10% or 25% of the thickness of the lead). The pressure plate 330 may be made of any suitable material including, for example, a metal such as titanium, nickel, aluminum, stainless steel, copper, gold, silver, platinum and alloys thereof, or a plastic, rubber or polymer such as polyurethane. In other embodiments (not shown), the fastener 320 directly contacts the lead 110 to lock it in position within the cover 202.

As shown in FIG. 3B, a septum 351 may be disposed over the fastener aperture 272 of the fastener pathway 242. The septum 351 may include silicone. It will be understood that the septum 351 may also be formed of any elastic, biocompatible material including, but not limited to, those suitable for the exterior member 310. In some embodiments, the septum 351 is formed of the same material as a member covering at least a portion of an outer surface of the cover 202. In at least some other embodiments, the septum 351 is a separate member that is attached, glued, fixed, or otherwise coupled to the cover 202. The septum 351 may cover the fastener pathway 242 to prevent the fastener 320 from separating from the anchoring unit 232. In some embodiments, the septum 351 includes a slit (or opening) to enable the tool 262 to reach the fastener 320. The slit may be large enough to receive the tool 262, but small to prevent the fastener 320 from separating from the anchoring unit 232.

FIG. 4 is a schematic cross-sectional view of the anchoring unit 232 of FIG. 3A after the lead 110 has been inserted in the anchoring unit. As can be appreciated from FIG. 4, as the fastener 320 is tightened, the pressure plate 330 is brought in contact with the lead 110 within the lead pathway 222. When the fastener 320 is completely tightened, the lead 110 is locked in place within the cover 202. In some embodiments, the lead 110 is partially deformed when locked in place.

Figure 5:
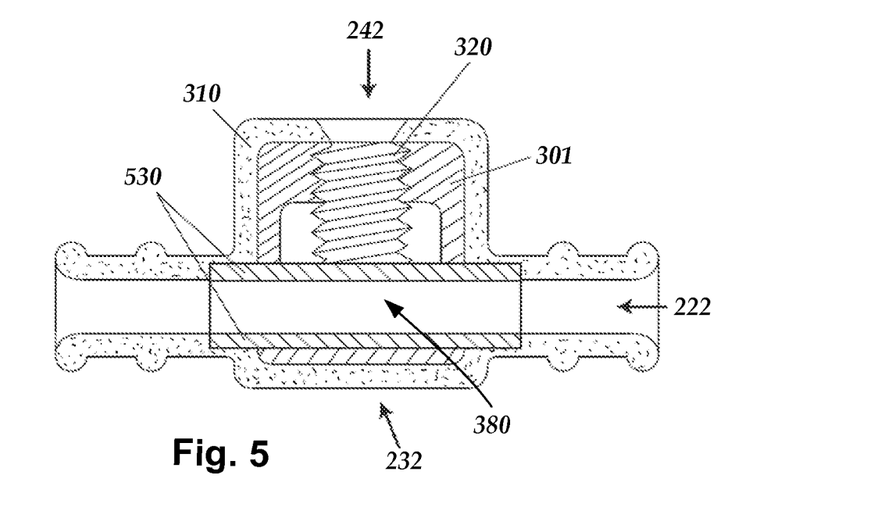
FIG. 5 is a schematic cross-sectional view of one embodiment of an anchoring unit with a sleeve, according to the invention.

FIG. 5 is a schematic cross-sectional view of another embodiment of the anchoring unit 232 with a sleeve 530. As shown in FIG. 5, in at least some embodiments, the sleeve 530 is disposed in the lead pathway 222 at the anchoring location 380. The sleeve 530 may be a substantially hollow cylinder or sheath, and may be made of any suitable material, for example, a metal such as titanium, nickel, aluminum, stainless steel, copper, gold, silver, platinum and alloys thereof, or a plastic, rubber or polymer such as polyurethane. In other embodiments, the fastener 320 directly contacts the lead 110 to lock it in position within the cover 202.

In some embodiments, the sleeve 530 is permanently disposed at the anchoring location 380 and receives the lead 110 when the lead 110 extends along the lead pathway 222. In another embodiment, the sleeve 530 is removable and is placed around the lead 110 before the lead 110 is inserted into the cover 202. In some embodiments, the sleeve 530 is deformable when the fastener 320 is tightened. The deformation of the sleeve 530 may be slight (e.g., no more than 5% or 10% of the thickness of the sleeve 530) or more significant (e.g., at least 10% or 25% of the thickness of the sleeve 530).

Figure 6:
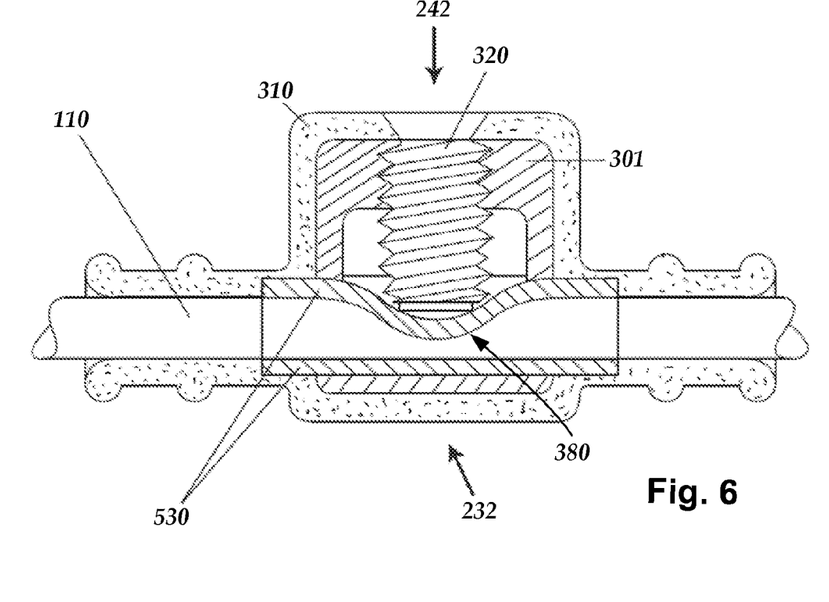
FIG. 6 is a schematic cross-sectional view of the anchoring unit of FIG. 5 after a lead has been inserted in the anchoring unit, according to the invention.

FIG. 6 is a schematic cross-sectional view of one embodiment of the anchoring unit 232 with the sleeve 530 after the lead 110 has been inserted in the lead pathway 222. As the fastener 320 is tightened, the sleeve 530 is deformed and partially obstructs the lead pathway 222. When the lead 110 is placed within the lead pathway 222 and the fastener 320 is tightened, the sleeve 530 closes down on the lead 110 to keep the lead 110 in place. In at least some embodiments, the lead 100 is partially deformed when the sleeve 530 is acted upon by the fastener 320.

In at least some embodiments, implanting the lead 110 into the patient's brain at a position to achieve the desired effect at the chosen site of stimulation includes placing the cover 202 over a burr hole formed in the patient's skull and receiving the lead through the cover 202 such that the lead 110 extends along the lead pathway 222 and a distal end of the lead 110 extends into the patient's brain. In at least some embodiments, receiving the lead 110 through the cover 202 includes receiving the lead 110 such that the proximal end of the lead 110 extends from the first lead aperture 224 defined along the side exterior surface 216 of the cover 202, and the distal end of the lead 110 extends from the second lead aperture 226 defined along the bottom exterior surface 214 of the cover 202. After the distal end of the lead 110 has been positioned, as desired, the fastener 320 is tightened so that the lead 110 is locked in place within the cover 202. In at least some embodiments, tightening the fastener 320 involves extending the tool 262 along the fastener pathway 242 to access the fastener 320.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor assembly comprising:
  a burr hole cover configured and arranged for implanting over a burr hole formed in a skull of a patient, the burr hole cover having a top exterior surface, an opposing bottom exterior surface, and a side exterior surface coupling the top exterior surface to the bottom exterior surface, the burr hole cover defining a first lead aperture in the side exterior surface, a second lead aperture in the bottom exterior surface, and a fastener aperture;
  an anchoring unit disposed in the burr hole cover, the anchoring unit comprising a fastener configured and arranged for anchoring a lead to the burr hole cover;
  a lead pathway defined through the burr hole cover and the anchoring unit, the lead pathway extending from the first lead aperture to the second lead aperture, the lead pathway configured and arranged to receive a lead; and
  a fastener pathway defined through both the burr hole cover and the anchoring unit and intersecting the lead pathway at an anchoring location, the fastener pathway configured and arranged for movement of the fastener along the fastener pathway to engage and disengage the lead when the lead extends along the lead pathway across the anchoring location, wherein the anchoring unit further comprises a sleeve disposed at the anchoring location, the sleeve configured and arranged to receive the lead when the lead extends along the lead pathway across the anchoring location.

2. The lead anchor assembly of claim 1, wherein the fastener is configured and arranged for anchoring the lead to the anchoring unit by deforming a portion of the lead.

3. The lead anchor assembly of claim 1, wherein the lead pathway comprises a bend.

4. The lead anchor assembly of claim 3, wherein the bend of the lead pathway has an arc of at least 20°.

5. The lead anchor assembly of claim 3, wherein the burr hole cover has a diameter, and wherein the bend of the lead pathway has a radius of curvature that is at least one-fifth the diameter of the burr hole cover.

6. The lead anchor assembly of claim 1, wherein the lead pathway comprises a single bend.

7. A lead anchor assembly comprising:
  a burr hole cover configured and arranged for implanting over a burr hole formed in a skull of a patient, the burr hole cover having a to exterior surface, an opposing bottom exterior surface, and a side exterior surface coupling the top exterior surface to the bottom exterior surface, the burr hole cover defining first lead aperture in the side exterior surface, a second lead aperture in the bottom exterior surface, and a fastener aperture;
  an anchoring unit disposed in the burr hole cover, the anchoring unit comprising a fastener configured and arranged for anchoring a lead to the burr hole cover;
  a lead pathway defined through the burr hole cover and the anchoring unit, the lead pathway extending from the first lead aperture to the second lead aperture, the lead pathway configured and arranged to receive a lead; and
  a fastener pathway defined through both the burr hole cover and the anchoring unit and intersecting the lead pathway at an anchoring location, the fastener pathway configured and arranged for movement of the fastener along the fastener pathway to engage and disengage the lead when the lead extends along the lead pathway across the anchoring location, wherein the anchoring unit further comprises a pressure plate disposed at the anchoring location, the pressure plate configured and arranged to compress a portion of the lead when the lead extends along the lead pathway across the anchoring location.

8. A lead anchor assembly comprising:
  a burr hole cover configured and arranged for implanting over a burr hole formed in a skull of a patient, the burr hole cover having a top exterior surface, an opposing bottom exterior surface, and a side exterior surface coupling the top exterior surface to the bottom exterior surface, the burr hole cover defining a first lead aperture in the side exterior surface, a second lead aperture in the bottom exterior surface, and a fastener aperture;

an anchoring unit disposed in the burr hole cover, the anchoring unit comprising a fastener configured and arranged for anchoring a lead to the burr hole cover;

a lead pathway defined through the burr hole cover and the anchoring unit, the lead pathway extending from the first lead aperture to the second lead aperture, the lead pathway configured and arranged to receive a lead; and a fastener pathway defined through both the burr hole cover and the anchoring unit and intersecting the lead pathway at an anchoring location, the fastener pathway configured and arranged for movement of the fastener along the fastener pathway to engage and disengage the lead when the lead extends along the lead pathway across the anchoring location, further comprising a septum disposed over the fastener aperture, the septum preventing the fastener from disengaging from the fastener aperture.

9. The lead anchor assembly of claim 1, wherein the fastener comprises a set screw having a thread, and wherein the anchoring unit further comprises a thread complementary to the thread of the set screw, the complementary thread disposed along at least a portion of the fastener aperture.

10. The lead anchor assembly of claim 1, wherein the anchoring unit is formed as a continuous unit with the burr hole cover.

11. The lead anchor assembly of claim 1, wherein the anchoring unit is detachable from the burr hole cover.

12. An implantable electrical stimulation system, comprising:
a lead having a proximal end and a distal end, the lead comprising
a plurality of terminals disposed at the proximal end of the lead, and
a plurality of electrodes disposed at the distal end of the lead; and
the lead anchor assembly of claim 1.

13. The electrical stimulation system of claim 12, further comprising a control module coupleable to the proximal end of the lead.

14. The electrical stimulation system of claim 13, further comprising a lead extension configured and arranged for coupling the control module to the proximal end of the lead.

15. A method of implanting a lead of a deep brain stimulation system into a patient, the method comprising:
providing the lead anchor assembly of claim 1;
receiving the lead along the lead pathway of the burr hole cover with a proximal end of the lead extending from the first lead aperture of the burr hole cover and a distal end of the lead extending from the second lead aperture of the burr hole cover, wherein a plurality of electrodes are disposed on the distal end of the lead;
disposing the burr hole cover over a burr hole with the distal end of the lead disposed in the patient's skull;
tightening the fastener to secure the anchoring unit to the lead, wherein tightening the fastener deforms a portion of the lead at the anchoring location of the burr hole cover, wherein tightening the fastener comprises tightening the fastener onto a sleeve disposed at the anchoring location within the burr hole cover to secure the anchoring unit to the lead; and
securing the burr hole cover to the patient's skull.

16. The method of claim 15, further comprising implanting a control module in the patient, the control module electrically coupled to the plurality of electrodes via the lead.

17. A method of implanting a lead of a deep brain stimulation system into a patient, the method comprising:
providing the lead anchor assembly of claim 7;
receiving the lead along the lead pathway of the burr hole cover with a proximal end of the lead extending from the first lead aperture of the burr hole cover and a distal end of the lead extending from the second lead aperture of the burr hole cover, wherein a plurality of electrodes are disposed on the distal end of the lead;
disposing the burr hole cover over a burr hole with the distal end of the lead disposed in the patient's skull;
tightening the fastener to secure the anchoring unit to the lead, wherein tightening the fastener deforms a portion of the lead at the anchoring location of the burr hole cover, wherein tightening the fastener comprises tightening the fastener onto a pressure plate disposed at the anchoring location within the burr hole cover to secure the anchoring unit to the lead; and
securing the burr hole cover to the patient's skull.

18. The method of claim 15, wherein the fastener is a set screw, and wherein tightening the fastener comprises using a torque limiting tool to secure the set screw.

19. An implantable electrical stimulation system, comprising:
a lead having a proximal end and a distal end, the lead comprising
a plurality of terminals disposed at the proximal end of the lead, and
a plurality of electrodes disposed at the distal end of the lead; and
the lead anchor assembly of claim 7.

20. An implantable electrical stimulation system, comprising:
a lead having a proximal end and a distal end, the lead comprising
a plurality of terminals disposed at the proximal end of the lead, and
a plurality of electrodes disposed at the distal end of the lead; and
the lead anchor assembly of claim 8.

* * * * *